US008365582B2

(12) United States Patent
Sakai

(10) Patent No.: US 8,365,582 B2
(45) Date of Patent: Feb. 5, 2013

(54) DEVICE FOR MEASURING VISCOSITY/ELASTICITY AND METHOD FOR MEASURING VISCOSITY/ELASTICITY

(75) Inventor: Keiji Sakai, Tokyo (JP)

(73) Assignee: The University of Tokyo, Tokyo (JP)

( * ) Notice: Subject to any disclaimer, the term of this patent is extended or adjusted under 35 U.S.C. 154(b) by 274 days.

(21) Appl. No.: 12/989,612

(22) PCT Filed: Apr. 23, 2009

(86) PCT No.: PCT/JP2009/058089
§ 371 (c)(1), (2), (4) Date: Oct. 25, 2010

(87) PCT Pub. No.: WO2009/131185
PCT Pub. Date: Oct. 29, 2009

(65) Prior Publication Data

US 2011/0036150 A1 Feb. 17, 2011

(30) Foreign Application Priority Data

Apr. 25, 2008 (JP) ................................ 2008-116359

(51) Int. Cl.
*G01N 11/14* (2006.01)

(52) U.S. Cl. .................. 73/54.31; 73/64.49; 73/862.381

(58) Field of Classification Search ........................ None
See application file for complete search history.

(56) References Cited

U.S. PATENT DOCUMENTS 5,394,739 A * 3/1995 Garvey et al. ................ 73/54.23
6,546,866 B1 4/2003 Adachi et al.
6,691,560 B2 * 2/2004 Abnett ......................... 73/54.28
2003/0084708 A1 * 5/2003 Abnett ......................... 73/54.28
2012/0130152 A1 * 5/2012 Ozaki et al. ..................... 600/16

FOREIGN PATENT DOCUMENTS

| | | | |
|---|---|---|---|
| JP | 59-221639 | | 12/1984 |
| JP | 63-12936 | A | 1/1988 |
| JP | 01-263533 | A | 10/1989 |
| JP | 2001-343316 | A | 12/2001 |
| JP | 2005-069872 | A | 3/2005 |
| JP | 2008-080888 | A | 4/2008 |

OTHER PUBLICATIONS

M. Bano et al., "A viscosity and density meter with a magnetically suspended rotor" Review of Scientific Instruments, Nov. 2003, vol. 74, No. 11, pp. 4788-4793.

Office Action mailing date of Jun. 12, 2012 on the underlying Application No. 2008-116359 with English translation thereof.

* cited by examiner

*Primary Examiner* — Andre Allen
(74) *Attorney, Agent, or Firm* — Kenyon & Kenyon LLP

(57) ABSTRACT

An apparatus of measuring viscosity and/or elasticity comprising: an electro-conductive rotor; a container that contains a sample and the rotor such that the rotor is arranged in the sample; a magnet unit that is arranged in the surrounding of the container and applies a magnetic field to the rotor; a rotation controlling unit that drives the magnet unit to apply a rotating magnetic field to the rotor so as to induce induced current in the rotor and rotate the rotor by providing the rotor with a rotation torque caused by Lorentz interaction between the induced current and the magnetic field applied to the rotor; a rotation detection unit that detects the rotation of the rotor; and a dynamic property detection unit that detects viscosity and/or elasticity of the sample being in contact with the rotor based on the rotation torque and the rotational movement.

17 Claims, 2 Drawing Sheets

DEVICE FOR MEASURING VISCOSITY/ELASTICITY AND METHOD FOR MEASURING VISCOSITY/ELASTICITY

TECHNICAL FIELD

The present invention relates to an apparatus of measuring dynamical properties, specifically viscosity and elasticity of materials, and a method of measuring viscosity and/or elasticity.

Priority is claimed on Japanese Patent Application No. 2008-116359 filed on Apr. 25, 2008, the content of which is incorporated herein by reference.

BACKGROUND ART

Measurement of viscosity and/or elasticity of materials is an inevitable technique for quality control, performance evaluation, materials control, and research and development related to production of various materials including medicines, foods, coatings, inks, cosmetics, chemicals, chemical products, adhesives, fiber, plastics, drinks (for example, beer), detergents, concrete admixture, and silicone or the like. Therefore, measurements of viscosity and/or elasticity of materials have been performed in the prior art so as to detect dynamical properties of the objective materials (for example, see Patent Reference 1).

The following methods of measuring viscosity have been known in the prior art:

(1) In the viscosity tube method, viscosity of a fluid is measured based on a velocity of the fluid flowing down in a tube.

(2) A method of measuring viscosity, where an oscillator makes contact with a sample, and the viscosity of the sample is measured based on the change of the amplitude of the oscillator.

(3) A method of measuring viscosity based on a propagation property of surface acoustic wave.

(4) A method of measuring viscosity, where a rotor is rotated in a sample, and a viscosity is measured based on direct measurement of torque generated by viscous resistance.

(5) A method of measuring viscosity based on a duration of falling of a rigid sphere falling in a sample fluid.

(6) In a dynamic light scattering method, the viscosity of a material is measured based on a diffusion coefficient obtained by measurement of dynamic scattering of laser light irradiated to particles under Brownian motion.

(7) In a Zimm type viscosity measurement, a probe floating in the sample is rotated, and the viscosity is measured based on the rotation torque of the probe.

Prior Art Reference

Patent Reference 1: Japanese Unexamined Patent Application, First Publication, No. 2005-69872.

DISCLOSURE OF THE INVENTION

Problems to be Solved by the Invention

The methods of measuring viscosity described in the above (1) to (5) included a problem in that large amount of sample having a volume of several cc or more was required for measuring the viscosity.

In the methods described in the above (2) to (5), a sample must have a viscosity of at least 10 cP or more for performing precise measurement of the viscosity. Therefore, viscosity of a low-viscosity material could not be measured by these methods.

Further, the method described in (6) includes a problem in that a large apparatus is required, and that the method cannot be applied to a material other than a transparent material.

In the method described in the above (7), the ripple of a sample surface is caused by the rotation of the probe floating on the surface by a buoyancy, resulting in non-negligible energy loss. In addition, where a molecule absorption film is formed on the sample surface, the surface elasticity of the film causes an error of measurement. Since the rotation of the probe depends on a length of a portion sinking (dipped) in the sample, it is necessary that a density of the sample is already known.

Further, in any of the methods described in (1) to (7), sample container is expensive, and therefore, reuse of the container is required. Therefore, it is necessary to clean the container after the measurement. Unless the previously measured sample is removed completely, it is impossible to perform precise measurement due to the influence of the residual sample.

That is, in a method of measuring viscoelasticity generally used in the prior art, at least a certain amount of sample has been required to perform measurement with a predetermined precision.

In addition, precision of measurement has been deteriorated for a sample having a viscosity smaller than 100 cP. Further, in a measurement using a rotation type viscometer or light-scattering, it was impossible to perform the measurement simply due to requirements for a large sized apparatus.

Viscosity and elasticity are general physical quantities of liquids and other soft materials. Based on the above-described reason, it has been difficult to measure the viscosity and/or elasticity simply using a small amount of sample by a method according to the conventional principle. In addition, it has been difficult to measure viscosity and/or elasticity of a sample of low viscosity with high precision. Further, there has been a restriction on measurement efficiency, for example, due to a requirement for cleaning of measuring container.

Based on the above-described circumstance, an object of the present invention is to provide an apparatus of measuring viscosity and/or elasticity and a method of measuring viscosity and/or elasticity whereby viscosity and/or elasticity can be measured using a relatively small amount of sample compared to the conventional method, using a small and simple apparatus, and using a disposable inexpensive container for containing a material to be measured.

Solutions to the Problems

An apparatus of measuring viscosity and/or elasticity (apparatus of measuring dynamical properties) according to the present invention includes: an electro-conductive rotor; a container that contains a sample (a sample subjected to detection of viscosity and/or elasticity) and the rotor such that the rotor is arranged in the sample; a magnet unit (magnets) that is arranged in the surrounding of the container and applies a magnetic field to the rotor; a rotation controlling unit that drives the magnet unit to applies a rotating magnetic field to the rotor so as to induce induced current in the rotor and rotate the rotor by providing the rotor with a rotation torque caused by Lorentz interaction between the induced current and the magnetic field applied to the rotor; a rotation detection (determination) unit that detects the rotation (rotational movement) of the rotor; and a dynamic property detection unit (viscosity/elasticity detection unit) that detects (determines) the viscosity and/or elasticity of the sample being in contact with the rotor based on the rotation torque and the rotational movement of the rotor.

The viscosity detected in the above-described apparatus may be expressed by a viscosity coefficient of the sample.

The elasticity detected in the above-described apparatus may be expressed by an elasticity coefficient.

The above described apparatus of measuring viscosity and/or elasticity may be configured such that the rotation detection unit detects a rotation frequency (cycle) of the rotor and the dynamic property detection unit detects viscosity of the sample based on the rotation torque and the rotation frequency.

The above described apparatus of measuring viscosity and/or elasticity may be configured such that the rotation detection unit detects a rotation angle from the initial static position of the rotor before being provided with the rotation torque to an equilibrium static position of the rotor at which the rotor stops by the balance between the rotation torque and the elastic resistance of the rotor, and the dynamic property detection unit detects elasticity of the sample based on the rotation torque and the rotation angle of the rotor.

The above-described apparatus of measuring viscosity and elasticity may be configured such that the apparatus further includes a storage unit (memory unit) that stores standard data obtained by preliminary measurement of relationships between rotation torques and rotation frequencies of the rotor in a plurality of materials (standard samples) having known viscosities, and the physical property detection unit detects viscosity of the sample by comparing the standard data and a detected relationship between the rotation torque and the rotation frequency of the rotor in a sample.

The above-described apparatus of measuring viscosity and elasticity may be configured such that the apparatus further includes a storage unit that stores standard data obtained by preliminary measurement of relationships between rotation torques and rotation angles of the rotor in a plurality of materials having known elasticities, and the physical property detection unit detects the elasticity of the sample by comparing the standard data and a detected relationship between the rotation torque and the rotation angle of the rotor in a sample.

The above-described apparatus of measuring viscosity and elasticity may be configured such that the rotor is provided with a mark, and the rotation detection unit detects the rotation of the rotor by detecting the mark of the rotor.

The above-described apparatus of measuring viscosity and elasticity may be configured such that at least a partial portion of a bottom of the rotor is in contact with a bottom portion of an inner surface of the container, and the bottom portion of the inner surface of the container in contact with the rotor is a smooth plane or a smooth concave curved surface, and the bottom portion of the rotor has a smooth convex curved surface.

The above-described apparatus of measuring elasticity and viscosity may be configured such that a radius of the rotor is determined by the following formula, $$R < \frac{3}{2}\frac{\omega\eta\beta}{\alpha\Delta\rho\mu g}$$

where R denotes a radius of the rotor, g denotes a gravitational acceleration, ω denotes an angular velocity, η denotes a viscosity coefficient, Δρ denotes a difference of density between a lower portion of the rotor and the sample, μ denotes a frictional coefficient between the lower portion of the rotor and the bottom portion of the container, and α and β denote coefficients.

Here, R may be determined by substituting the viscosity coefficient of a material (for example, material having a chemical composition substantially similar to the sample) which resembles the sample and has a known viscosity for the viscosity η. Alternatively, a provisional viscosity coefficient set at a value slightly higher (110 to 150%) than a viscosity coefficient of a material which resembles the sample and has a known viscosity may be substituted for the viscosity coefficient η to determine R.

In the above-described apparatus of measuring viscosity and/or elasticity, a partial portion or a total portion of the rotor may sink in the sample.

In the above-described apparatus of measuring viscosity and/or elasticity, the sample may be a liquid or a soft material.

A method of detecting viscosity and/or elasticity according to the present invention may include: filling a sample (detection target) to be subjected to detection of viscosity and/or elasticity in a container and arranging an electro-conductive rotor in the sample; applying a magnetic filed to the rotor by a magnet unit arranged in the surrounding of the container; performing rotation control of the rotor by changing the magnetic field with time to induce induced current in the rotor and rotate the rotor by providing the rotor with a rotation torque caused by Lorentz interaction between the induced current and the magnetic field applied to the rotor; performing rotation detection of the rotor; and detecting dynamic property of the sample to detect viscosity and/or elasticity of the sample being in contact with the rotor based on the rotation torque and the rotational movement of the rotor.

The viscosity of the sample detected in the above-described method may be expressed by a viscosity coefficient.

The elasticity of the sample detected in the above-described method may be expressed by an elasticity coefficient.

The above-described method of measuring viscosity and/or elasticity may be configured such that the rotation control includes rotating the rotor, the rotation detection includes detecting a rotation frequency of the rotor, and the viscosity of the sample is detected based on the rotation torque and the rotation frequency.

The above-described method of measuring viscosity and/or elasticity may be configured such that the rotation control includes rotating the rotor from an initial static position (a position before applying the rotation torque) to a equilibrium static position (a position at which the rotor stops by the balance of the rotation torque between elastic resistance of the sample), the rotation detection includes detecting a rotation angle from the initial static position to the equilibrium static position, and the dynamic property detection includes detecting elasticity of the sample being in contact with the rotor based on the rotation torque and the rotation angle of the rotor.

The above-described method of measuring viscosity and/or elasticity may be configured such that the method further includes preparing standard data obtained by preliminarily measuring the relationships between rotation torques and rotation frequencies of the rotor in a plurality of materials (standard samples) having known viscosities, and the viscosity of the sample is detected by comparing the standard data and the relationship between the rotation torque and the rotation frequency of the rotor within the sample.

The above-described method of measuring viscosity and/or elasticity may be configured such that the method further includes preparing standard data by preliminary measurement of relationships between rotation torques and rotation angles of the rotor in a plurality of materials each having a known elasticity, and the elasticity of the sample is detected by comparing the standard data and the detected relationships between the rotation torque and the rotation angle of the rotor in a sample.

In the rotation control of above-described method of measuring viscosity and/or elasticity, the magnetic field may be controlled to be a rotational magnetic field where a horizontal direction of the magnetic field (horizontal component of the direction of the magnetic field) rotates with time.

In the above-described method of measuring viscosity and/or elasticity, the rotor may have a specific weight larger than the specific weight of the sample.

Effect of the Invention

As explained above, according to the present invention, the viscosity and/or elasticity of a sample is measured based on the relationship between the rotation torque applied to the rotor that is rotated being in contact with the sample and the rotational movement of the rotor. Therefore, viscosity widely ranging from low viscosity to high viscosity may be measured using a small amount of a target sample. In addition since the viscosity and/or elasticity of a sample is detected by rotating the rotor by applying a magnetic filed to the rotor, measuring the rotation frequency of the rotor, detecting the viscosity of the sample based on the relationship between the rotation torque and the rotation frequency, and detecting elasticity of the sample based on a relationship between the rotation torque and the rotation angle of the rotor. Therefore, it is possible to measure viscosity and/or elasticity using an apparatus having a simple constitution compared to the conventional case. Further, it is possible to utilize a general test tube or the like as a sample container and make the container disposable. Therefore, it is possible to perform highly precise measurement while omitting cleaning of the container and while avoiding influence of a material which has been contained in the container just before the measurement.

EMBODIMENT FOR CARRYING OUT THE INVENTION

Figure 1:
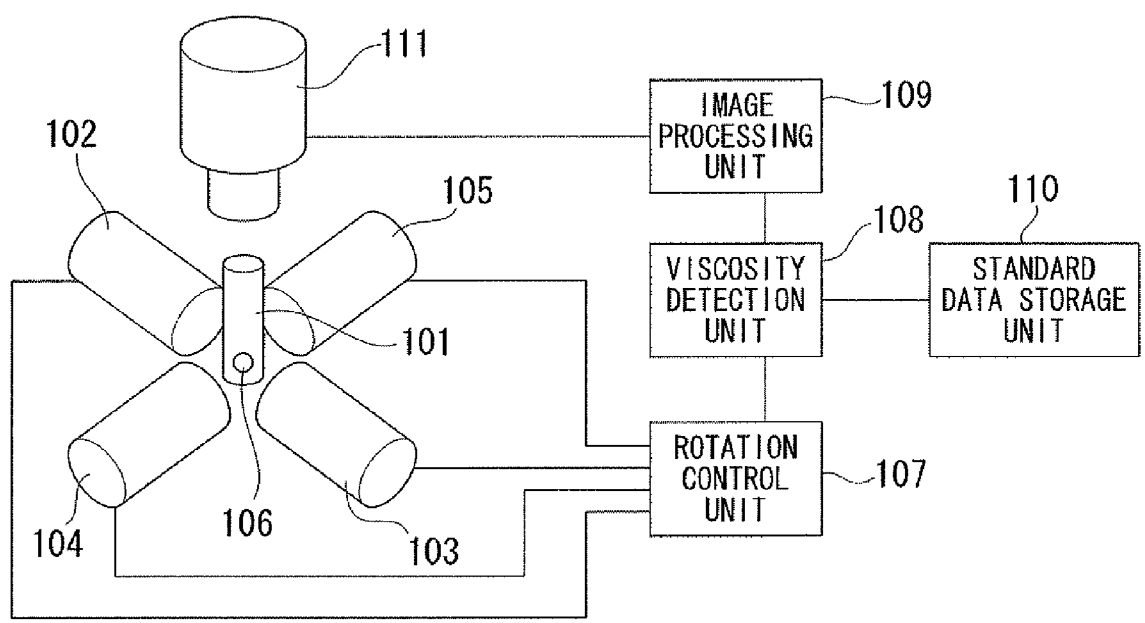
FIG. 1 is a block diagram showing an example of a constitution of an apparatus of measuring viscosity and/or elasticity according to an embodiment of the present invention.

In the following, an apparatus of measuring viscosity and/or elasticity according to an embodiment of the present invention is explained with reference to drawings. FIG. 1 is a block diagram showing an example of a constitution of the apparatus of measuring viscosity and/or elasticity of the embodiment.

In this figure, a container 101 is, for example, a small test tube or the like. A target sample is contained in the container 101 to measure a viscosity (viscosity coefficient) as a dynamical property of the sample. It is acceptable that the inner diameter of the container 101 is slightly larger than the inner diameter of the rotor 106. It is acceptable that the depth of sample (target material) contained in the container 101 for measurement is just sufficient for making the rotor 106 sink in the sample. Therefore, the measurement can be performed using an extremely small amount of a sample. For example, where a conductive sphere of 1 mm is used as the rotor 106, the sample in an amount of 100 micro-liter satisfies a necessary amount of measurement. Here, the rotor 106 may partially or totally sink in the sample that is a detection target material.

The rotor 106 is constituted of a conductive material (for example, metal such as aluminum) and has a shape having a smooth convex curved surface in the lower part thereof that is made to contact the container 101. For example, the rotor 106 may have a spherical or semi-spherical shape. That is, a partial surface of the rotor 106 in contact with the inner bottom face (bottom portion of the inner surface) of the container 101 may be constituted of a partial portion of a spherical surface. The rotor 106 may have a spheroidal shape. The rotor 106 is arranged in the container 101 such that the rotor 106 is made to contact the detection target material within the material. That is, the rotor 106 is arranged such that a partial portion or a total portion of the rotor 106 sink in the detection target. The inner bottom face of the container 101 being in contact with the rotor 106 may be a smooth plane or may have a smooth concave curved surface.

It is possible to use commercial metal spherule as the rotor 106. By using such a rotor 106 with a commercial test tube as the container 101, it is possible to constitute the parts of the apparatus in contact with the sample by disposable members. Therefore, even in the measurement of a material (for example, biomaterials) which requires a specific duty in disposition, it is possible to easily perform after treatment such as incineration and sterilization.

According to the present invention, it is possible to measure the viscosity and/or elasticity of a small amount of sample using a small rotor. For example, the rotor may be a metal spherule having a diameter of not more than 1 cm, or a diameter of not more than 2 mm. According to the present invention, it is possible to perform measurement of the viscosity and/or elasticity of a sample of 100 to 500 micro-liter in volume.

Electromagnets 102, 103, 104, and 105 are arranged in the surrounding (circumference) of the container. A pair A of electromagnet 102 and electromagnet 103 are arranged in line interposing the container 101 on a plane perpendicular to the lengthwise direction of the container.

A pair B of electromagnet 104 and electromagnet 105 are arranged interposing the container 101 in the same plane as the pair A in a line perpendicular to the alignment of pair A.

That is, where lengthwise direction of the container 101 is arranged along a z-axis of a rectangular coordinate system, the pair A may be arranged along a x-axis, and the pair B may be arranged along a y-axis.

For example, the container 101 may be arranged such that its lengthwise direction is along a vertical direction, and the pair A and the pair B of the electric magnets may be arranged on a horizontal plane.

The electric magnets 102, 103, 104, and 105 are connected to a rotation control unit 107. The rotation control unit alternately energize the pair A and the pair B of the electric magnets, thereby generating a magnetic field in a direction which changes alternately with time between two directions (direction of x-axis and direction of y-axis) perpendicular to each other.

For example, electric magnet 104 and electric magnet 105 of the pair B are not energized during the time in which the electric magnet 102 and the electric magnet 103 of the pair A are energized (that is, during electrifying of the coils of the electric magnet 102 and the electric magnet 103) by the rotation control unit 107. The electric magnet 102 and electric magnet 103 of the pair A are not energized during the time in which the electric magnet 104 and the electric magnet 105 of the pair B are energized.

By the above-described control of electric magnets, the rotation control unit 107 applies rotating magnetic field to the rotor 106 thereby inducing induced current in the rotor 106. By the Lorentz interaction between the induced current and the magnetic field applied to the rotor 106, the rotor 106 is provided with a rotation torque and is rotated.

A dynamic property detection unit 108 commands a time cycle of the alternate energizing of the magnets to the rotation control unit 107.

In the above-described constitution, rotating magnetic field is applied to the rotor 106 by using electric magnets and energizing the coils of the electric magnets sequentially.

As an alternative embodiment, a pair of permanent magnets may be arranged in line interposing the container 101. A rotation torque may be provided to the rotor 106 by rotating the permanent magnets around the container 101 using a motor or the like, thereby applying a rotating magnetic field to the rotor 106. In this case, the rotation frequency of the permanent magnets is controlled by the rotation control unit 107 depending on a command from the dynamic property detection unit 108.

A image processing unit 109 may be, for example, constituted of an imaging device (CCD) equipped with a microscope. The image processing unit 109 is arranged above an opening of the container 101. The image processing unit 109 measures the rotation frequency of the rotor 106 by detecting the rotation of the mark provided to the rotor 106. Therefore, the image processing unit 109 is arranged above the container 101 such that an alignment of imaging direction allows detection of the mark on an upper surface of the rotor 106.

Standard data showing relationships between the rotation torque applied to the rotor 106 and the rotation frequency of the rotor 106 in a plurality of standard samples of different viscosity are stored in a standard data storage unit 110.

Standard data may be preliminarily obtained by filling each standard sample in the container 101, rotating the rotor 106, and recording the rotation torque applied to the rotor 106 and the rotation frequency of the rotor 106.

In the measurement of each standard sample, the rotation torques are calculated for each rotation frequency while changing the rotation frequency to obtain a primary curve approximated by the below described formula (8). The inclination of the primary curve is determined and stored as a part of the standard data.

The dynamic property detection unit 108 is connected to the image processing unit 109 and the standard data storage unit. The dynamic property detection unit 108 acquires data of the rotation frequency of the rotor 106 output from the image processing unit 109 and the rotation torque corresponding to the rotation frequency. Next, an inclination of the primary curve shown by the below-described formula (8) is determined for the detection target, the ratio of the inclination to the inclination of standard data read from the standard data storage unit 110 is determined. That is, the inclination of the primary curve of the standard data is divided by an inclination of the primary curve of the detection target, and the viscosity of the standard sample is multiplied by the ratio of the inclinations, thereby calculating the viscosity $\eta$ of the detection target.

In this time, the dynamic property detection unit may determine the viscosity of detection target based on a plurality of standard data. For example, the dynamic property detection unit 108 may read inclinations of primary curves of a plurality of different standard samples stored in the standard data storage unit 110. In this case, for each of the standard data, the inclination of the primary curve of the standard datum is divided by the inclination of the primary curve of the detection target, and the viscosity of the corresponding standard datum is multiplied by the ratio of the inclinations, thereby calculating the viscosity $\eta$ of the detection target. The viscosity of the detection target may be determined as an average value of viscosities determined based on the plurality of standard data.

In the following, a principle of measuring viscosity based on the rotation torque applied to the rotor 106 and the rotation frequency of the rotor 106 is explained.

Here, so as to make an explanation based on a rectangular coordinate system, lengthwise direction of the container is regarded as a direction parallel to the z-axis, and arrangement of the pair A is regarded as a direction parallel to the x-axis, and arrangement of the pair B is regarded as a direction parallel to the y-axis.

For example, magnetic field parallel to the x-axis expressed by $B=(B_0 \cos \omega t, 0,0)$ may be generated around the container 101 by the electric magnets 102 and 103 of the pair A. Magnetic field parallel to the y-axis expressed by $B=(0, B_0 \sin \omega t, 0)$ may be generated by the electric magnets 104 and 105 of the pair B. Here, $B_0$ denotes the maximum value of the magnetic field intensity, $\omega$ denotes angular velocity, and t denotes a time.

By the magnetic filed B changing with time (rotating magnetic filed), the electric field is generated in the conductive rotor 106 such that rot $E=-(dB/dt)$ is satisfied.

This electric filed is calculated as below-described formula (1)

$$E = \frac{\omega B_0}{2}(-z\cos\omega t,\ -z\sin\omega t,\ x\cos\omega t + y\sin\omega t) \tag{1}$$

By the electric field, electric current I is generated in the rotor 106 made of a conductive material such that $I=\sigma E$ is satisfied, where $\sigma$ denotes a conductivity of the conductive material. By the Lorentz interaction between the current I and the electric field B, a force F (Lorentz force) expressed by the below formula (2) functions in the rotor 106.

$$F = \frac{\omega B_0^2\sigma}{2}(-(x\cos\omega t + y\sin\omega t)\sin\omega t,\ (x\cos\omega t + y\sin\omega t)\cos\omega t,\ 0) \tag{2}$$

Radial component of the above-described F around an rotation axis perpendicular to the rotation plane of the rotor 106 can be calculated as the below-described formula (3) by integration of change with time for 1 cycle, $$F_\theta = \frac{\pi\omega\sigma B_0^2}{2} r,\ r = \sqrt{x^2 + y^2} \tag{3}$$

The force $F_\theta$ expressed by the above-described formula (3) acts as a force that rotates the rotor 106 around a vertical rotation axis. The torque T is expressed by the following formula (4), $$T = \int_{sphere} dV F_\theta r,\ r = \sqrt{x^2+y^2} \tag{4}$$

The rotor is rotated by the torque. However, the rotation velocity is controlled by two factors: one is a friction between the rotor 106 and a bottom portion of the container 101, and the other factor is the viscosity resistance of the detection target being in contact with the rotor 106.

To obtain the viscosity of the detection target in contact with the rotor 106 precisely, it is necessary that a resistance caused by the friction force in the bottom portion of the container 101 is substantially the same (similar value) or smaller than the viscosity resistance of the detection target.

To simplify the formula, radius of the rotor 106 perpendicular to the rotation plane of the rotor 106 is expressed by R, and a radius of an effective contact area of the lower surface of the rotor being in contact with the bottom face of a container is expressed by $\alpha R (\alpha<1)$.

In the effective contact radius, stress by the gravity applied to the rotor 106 is approximated to be constant.

A friction coefficient between the lower portion of the rotor 106 and the bottom portion of the container 101 is expressed by μ, difference of density between the rotor 106 and the detection target is expressed as Δp, and the gravity acceleration is expressed as g. The torque $T_f$ required to rotate the sphere overcoming the friction is calculated by the below-described formula (5).

$$T_f = \frac{8\pi}{9}\alpha\mu\Delta\rho g R^4 \tag{5}$$

The torque Tr required to rotate the rotor 106 with an angular velocity ω in an infinite space filled with the detection target is expressed by the below described-formula (6), where η denotes a viscosity coefficient.

$$T_r = \frac{4}{3}\pi R^3 \omega\eta \tag{6}$$

Where the lower portion of the rotor 106 is in contact with a planar or curved bottom face of the container 101, required torque $T_f$ is further enlarged. Where the enlarging coefficient is expressed by β,β is a value in the order of 1 but is larger than 1. β includes a coefficient of indirect interaction between the rotor 106 and side wall of the container during the rotation of detection target caused by the rotation of the rotor 106. Up to the formula (6), β is set to be β=1.

Based on the above-described calculations, it is understood that a condition of $T_r > T_f$ must be satisfied for the viscosity resistance to act stronger than the frictional force. The torque $T_f$ is proportional to 4th power of R, and the torque $T_r$ is proportional to 3rd power of R. Therefore, the above-described condition can be satisfied if a sufficiently small R is selected.

That is, conditions for measuring the viscosity of a liquid having a viscosity coefficient η is determined by the following formula (7), $$R < \frac{3}{2}\frac{\omega\eta\beta}{\alpha\Delta\rho\mu g} \tag{7}$$

In many cases, a target material (sample) of viscosity measurement is formed by modifying properties of known material. Therefore, the conditions related to R can be determined by substituting η of the above-described formula by a viscosity coefficient of a known material resembling the sample (for example, material having a chemical composition similar to the sample), or a value of about 110 to 150% of the viscosity coefficient of the known material.

For example, where η is set at $\eta=10^{-3}$ Pas assuming that the detection target is water, Δp is set at about 2000 kg/m$^3$ assuming that the rotor 106 is an aluminum sphere, α is set at about 1/100, β is set at about 1, and μ is set at about 0.1, the condition of R is R<1 mm where the angular velocity ω is about 10 rad/s allowing about 1 rotation per second.

The torque Tr applied to the aluminum sphere is proportional to a difference between the rotation velocity of the magnetic field (rate of changing the magnetic field alternately between x direction and y direction while energizing the pair A and pair B alternately) and the actual rotation velocity of the aluminum sphere.

Therefore, rotation torque T applied to the sphere can be estimated where the rotation velocity of the magnetic field is determined preliminarily and the rotation velocity of the sphere is measured.

It is possible to use the formula (4) in the calculation of the rotation torque T. Alternatively, it is possible to used a calibration curve (inclination of standard data stored in the standard data storage unit 110) obtained using standard samples with known viscosities.

The thus obtained torque T is expressed by the below-described formula (8), $$T = \frac{4}{3}\pi\beta R^3\omega\eta + \frac{8\pi}{9}\alpha\mu\Delta\rho g R^4 \tag{8}$$

As shown by the formula, the relation between the applied torque T and angular velocity ω is expressed as a primary curve that passes an intercept. That is, where the angular velocity ω is plotted along the horizontal axis, and torque T is plotted along the vertical axis, the curve may be expressed as a curve that intersects the vertical axis at a point where the second term of the formula (8) denotes the intercept. The torque due to the friction is determined based on the intercept (second term of the formula (8)), and viscosity η (first term of the formula (8)) is determined based on the inclination. The angular velocity ω can be determined based on the measured rotation frequency.

An inclination of the primary curve of the formula (8) expressed by the relationships between the rotation frequency of the rotor 106 and the quantities proportional to the rotation torques in the standard samples measured by the apparatus of measuring viscosity and/or elasticity, that is, the ratio of change of rotation torque to the rotation frequency is recorded in the standard data storage unit 110. These data are recorded with a value of viscosity for a plurality of standard samples having different viscosities.

In the observation of the rotational movement of the rotor 106, rotation frequency of the rotor 106 is measured by detecting rotation of the mark on the rotor 106 using an imaging device 111 equipped with a microscope as shown in FIG. 1.

The measurement of rotation frequency may be performed by another method. For example, as an alternative method, laser light may be irradiated to the rotor 106, and change of reflection and interference pattern due to the rotation may be measured optically. Alternatively, a portion of the rotor 106 may be replaced by a dielectric material to constitute a condenser where the rotor is interposed between electrodes, and rotation frequency of the rotor 106 may be measured by a periodic change of dielectric constant of the condenser due to rotation of the rotor 106.

As an alternative to the observation by the imaging device 111, the container 101 may be made of a transparent material, and observation may be performed from the bottom of the container 101 using an inverted microscope. In this case, the observation may be performed interposing a thin layer of the detection target between the bottom face of the container 101 and the lower portion of the rotor 106. Therefore, it is possible to perform the measurement even when the detection target is a material such as an ink material that scarcely transmits light. In this case, the mark for detecting the rotation frequency is provided to the lower part of the rotor 106.

The periodic cycle and direction of the magnetic field applied by the rotation control unit 107 to the rotor 106 may be changed arbitrarily.

For example, by periodically scanning the direction of the magnetic field and the rotation velocity, it is possible to apply a periodic rotation torque to the rotor 106.

In addition to the viscosity, it is possible to determine the elasticity simultaneously for materials such as gel or gum having viscosity and/or elasticity, or macromolecular solution occurring elasticity in accordance with relaxation of viscosity. The measurement may be performed based on a static position of the rotor in the material given a predetermined torque.

Elastic modulus provides restoring force proportional to the rotation deformation like in the case of spring constant. Therefore, when the material has elasticity in addition to the viscosity, the restoring force due to the elasticity increases in proportion to the strain. Therefore, after a rotation to sum extent, the rotor 106 stops by the balance of the elastic force (elastic resistance) and the torque given by the magnetic field.

The strength of the rotation torque applied to the rotor 106 is changed by changing the strength of the rotating magnetic field generated by the electric magnets 102 to 105, and changing the rotation velocity. By measuring an equilibrium static position of the rotor 106, the rotation angle from the initial state not applied with the rotation torque to the static position is detected. The rotation angle is proportional to the applied rotation torque, and the proportional coefficient is inversely proportional to the elastic modulus. Based on this relationship, it is possible to determine the elastic modulus. In this case, like in the case of measurement of viscosity, standard samples of known elasticity are used. The proportional coefficient is determined for each standard sample based on the relationship between the rotation torque and the rotation angle. Then, the elastic modulus of detection target can be determined based on the ratio of the proportional coefficient determined for the target material (sample) and the proportional coefficients determined for the standard samples.

It is possible to determine the elastic modulus and viscosity modulus simultaneously by changing the rotation torque applied to the rotor 106 with time.

For example, where a motion of the rotor 106 is observed after immediately erasing applied magnetic field subsequent to the application of a predetermined rotation torque to the rotor 106, the rotor 106 oscillates by the elasticity of the sample, and the amplitude of the oscillation attenuates due to the viscosity modulus.

Elastic modulus and viscosity modulus may be determined based on the amplitude, period, and duration of the oscillation of the rotor 106 in the target material. For example, it is possible to determine an elastic modulus of detection target by comparing the amplitude, period, and duration of the oscillation of the rotor 106 in the target material and the amplitude, period, and duration of the oscillation of the rotor 106 in a standard sample.

By scanning the direction of the magnetic field and the rotation velocity periodically, it is possible to apply a periodic rotation torque to the rotor 106.

The viscosity and/or elasticity may be determined independently, by observing amplitude and phase of rotational oscillation of the rotor 106 while changing the period.

This observation detects an attenuation of after erasing the magnetic field as a frequency spectrum. Therefore, the principle of measurement is the same as the above-described method.

EXAMPLES

In the following, practical examples according to the present embodiment is explained. It should be noted that the present invention is not limited to the below explained examples.

The below described viscosity detection treatments were carried out using an apparatus of measuring viscosity and/or elasticity (dynamic property measuring apparatus) as shown in FIG. 1.

A glass test tube having an inner diameter of 7 mm and a height of 7 mm was used as a container 101. 0.4 cc of pure water at 20° C. was poured as a sample material (detection target) in the glass test tube.

The pure water had a viscosity of 1.0 cP. An aluminum sphere of 2 mm in diameter was dipped as the rotor 106 in the pure water.

Next, rotational magnetic field was generated by rotating two permanent magnets around the sample container.

Rotational motion of the aluminum sphere caused by rotation torque generated by the rotational magnetic field was detected by an imaging device 110, and the image was recorded on a video tape. After that, the rotation frequency of the aluminum sphere was determined by mage processing using a computer (image processing unit 109). That is, while changing the rotation velocity of the rotational magnetic field, the rotation velocity of the aluminum sphere was measured.

Figure 2:
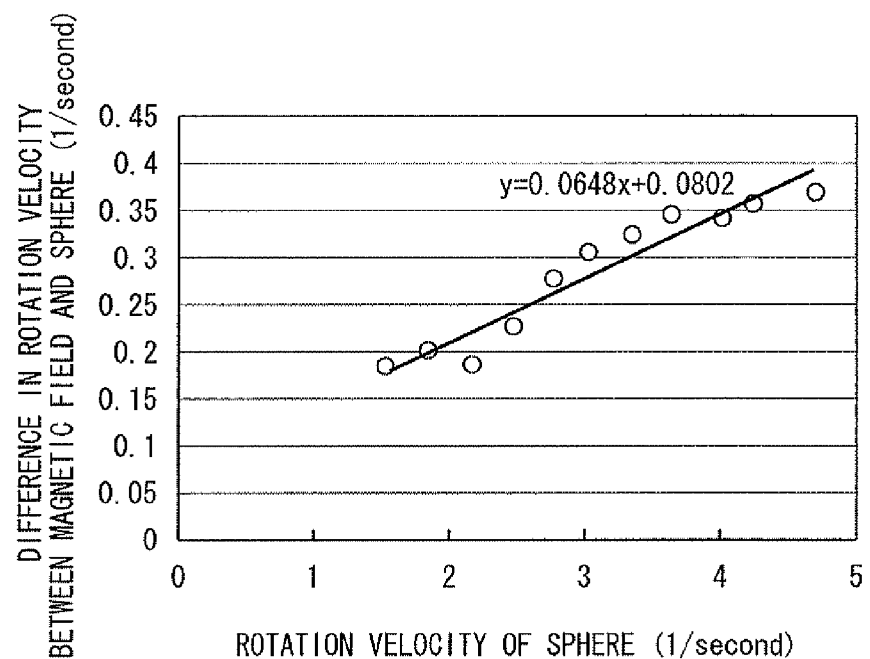
FIG. 2 is a graph showing the relationship between the rotation velocity (rotation frequency) of the rotor and the difference between the rotation velocity of the rotational magnetic field and the rotation velocity of the rotor (sphere), where the target sample is a water.

FIG. 2 shows a graph showing the relationship between the rotation frequency of the aluminum sphere and the difference (parameter proportional to the rotation torque) between the rotation velocity of the rotational magnetic field and the rotation velocity of the rotor 106. As described above, the difference of rotation velocity between the magnetic field and the rotating body is proportional to the rotation torque generated in the aluminum sphere.

Therefore, the vertical axis of the figure express a quantity proportional to the torque. The relationship is shown as a shape of primary function shown by the formula (8). Therefore, viscosity is determined by the inclination of the first term, and the frictional force is determined by the intercept (in the vertical axis) shown by the second term.

Further, the below-described operation was carried out using the dynamic property measuring apparatus shown in FIG. 1. A glass test tube having an inner diameter of 7 mm and a height of 7 mm was used as a container 101. 0.4 cc of aqueous solution of cane sugar of 30% by weight was poured as a sample material (detection target) in the glass test tube. The aqueous solution had a viscosity of 3.2 cP. An aluminum sphere of 2 mm in diameter was dipped as the rotor 106 in the aqueous solution. Next, a rotational magnetic field was generated by rotating two permanent magnets around the sample container 101.

Rotational motion of the aluminum sphere caused by rotation torque generated by the rotational magnetic field was detected by an imaging device 111, and the image was recorded on a video tape. After that, rotation frequency of the aluminum sphere was determined by mage processing using a computer (image processing unit 109). That is, while changing the rotation velocity of the rotational magnetic field, the rotation velocity of the aluminum sphere was measured.

Figure 3:
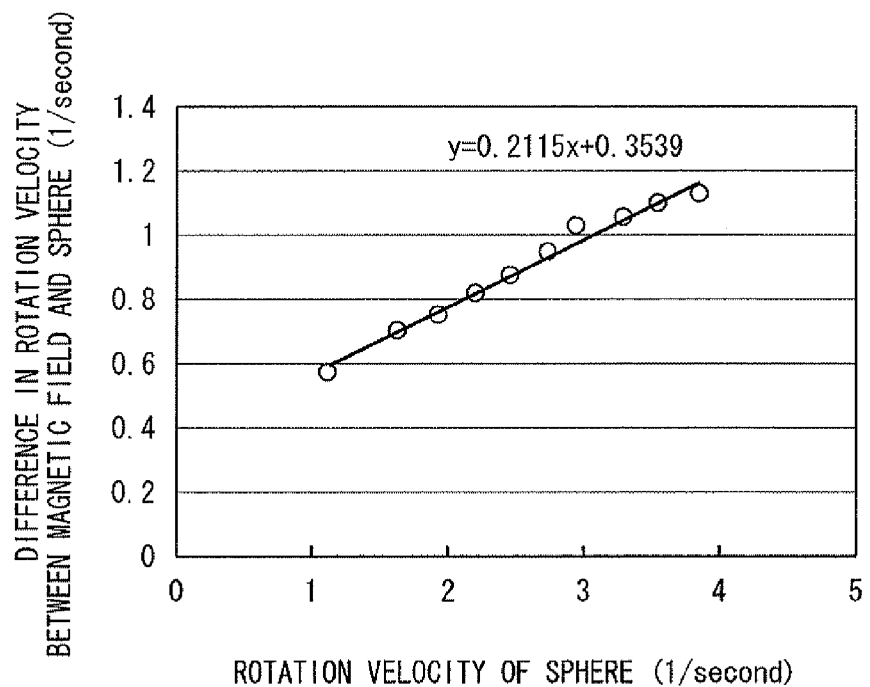
FIG. 3 is a graph showing the relationship between the rotation velocity (rotation frequency) of the rotor and the difference between the rotation velocity of the rotational magnetic field and the rotation velocity of the rotor (sphere), where the target sample is a cane sugar.

FIG. 3 shows a graph showing a relation between the rotation frequency of the rotating body and the difference between the rotation velocity of the rotational magnetic field and the rotation velocity of the rotor 106.

Compared to the pure water in FIG. 2, the graph shows large inclination due to large viscosity of the aqueous solution of cane sugar.

Rotation frequency of the rotational magnetic field in the intercept was about 0.4 rotation/second. This value is substantially in the same order as 1 rotation/second, that is a frictional force-consistent rotation frequency derived from formula (7) while assuming the viscosity to be 3 cP, and diameter of rotating body to be 2 mm. Therefore, the efficiency of the principle of the invention was confirmed.

The ratio of the inclination of FIG. 2 and the inclination of FIG. 3 was 3.26 which was consistent to the practical ratio of viscosities of 3.2. Therefore, it is understood that a viscosity in the order of 1 cP can be measured precisely.

In addition, based on the results, it is understood that the viscosity of a target material can be estimated by determining a ratio of inclinations of rotation torque to rotation frequency in the target material and a standard material, and multiplying a viscosity of the standard sample by the ratio.

INDUSTRIAL APPLICABILITY

According to the present invention it is possible to measure the viscosity and/or the elasticity of a small amount of a sample with high accuracy. At that time, it is possible to constitute the container and the rotor g in contact with the sample to be disposable by using commercial inexpensive articles. Therefore, it is possible to eliminate the influence of contamination by the other sample perfectly while reducing the cost required for the apparatus. In addition, it is possible to perform after-treatment related to the disposition of the sample easily and surely.

The invention claimed is:

1. An apparatus of measuring viscosity and/or elasticity comprising:

an electro-conductive rotor;

a container that contains a sample and the rotor such that the rotor is arranged in the sample;

a magnet unit that is arranged in the surrounding of the container and applies a magnetic field to the rotor;

a rotation controlling unit that drives the magnet unit to apply a rotating magnetic field to the rotor so as to induce induced current in the rotor and rotate the rotor by providing the rotor with a rotation torque caused by Lorentz interaction between the induced current and the magnetic field applied to the rotor;

a rotation detection unit that detects the rotation of the rotor; and a dynamic property detection unit that detects viscosity and/or elasticity of the sample being in contact with the rotor based on the rotation torque and the rotational movement.

2. The apparatus of measuring viscosity and/or elasticity according to claim 1, wherein the rotation detection unit detects a rotation frequency of the rotor, and the dynamic property detection unit detects viscosity of the sample based on the rotation torque and the rotation frequency.

3. The apparatus of measuring viscosity and/or elasticity according to claim 1, wherein the rotation detection unit detects a rotation angle from the initial static position of the rotor before being provided with the rotation torque to a equilibrium static position of the rotor at which the rotor stops by the balance of the rotation torque and elastic resistance of the rotor, and the dynamic property detection unit detects elasticity of the sample based on the rotation torque and the rotation angle of the rotor.

4. The apparatus of measuring viscosity and/or elasticity according to claim 2, further comprising a storage unit that stores standard data obtained by preliminary measurement of relations between rotation torques and rotation frequencies of the rotor in a plurality of materials having known viscosities, wherein the dynamic property detection unit detects viscosity of the sample by comparing the standard data and a detected relationship between rotation torque and rotation frequency of the rotor in a sample.

5. The apparatus of measuring viscosity and/or elasticity according to claim 3, further comprising a storage unit that stores standard data obtained by preliminary measurement of relationships between rotation torques and rotation angles of the rotor in a plurality of materials each having known elasticity, wherein the physical property detection unit detects elasticity of the sample by comparing the standard data and a detected relation between rotation torque and a rotation angle of the rotor in a sample.

6. The apparatus of measuring viscosity and/or elasticity according to claim 1, wherein the rotor is provided with a mark, and the rotation detection unit detects the rotation of the rotor by detecting the mark of the rotor.

7. The apparatus of measuring viscosity and/or elasticity according to claim 1, wherein at least a portion of a bottom portion of the rotor is in contact with a bottom portion of inner surface of the container, and the bottom portion of the inner surface of the container in contact with the rotor is a smooth plane or a smooth concave curved surface, and the bottom portion of the rotor has a smooth convex curved surface.

8. The apparatus of measuring viscosity and/or elasticity according to claim 1, wherein a radius of the rotor is determined by the following formula, $$R < \frac{3}{2}\frac{\omega\eta\beta}{\alpha\Delta\rho\mu g}$$

where R denotes a radius of the rotor, g denotes a gravitational acceleration, w denotes an angular velocity, η denotes a viscosity coefficient, Δp denotes a difference of density between the rotor and the sample, μ denotes a frictional coefficient between the lower portion of the rotor and the bottom portion of the container, and α and β denote coefficients.

9. The apparatus of measuring viscosity and/or elasticity according to claim 1, wherein a partial portion or a total portion of the rotor sink in the sample.

10. The apparatus of measuring viscosity and/or elasticity according to claim 1, wherein the sample is a liquid or a soft material.

11. A method of detecting viscosity and/or elasticity comprising:

filling a sample to be subjected to detection of viscosity and/or elasticity in a container and arranging an electro-conductive rotor in the sample;

applying a magnetic filed to the rotor by a magnet unit arranged in the surrounding of the container;

controlling a rotation of the rotor by changing the magnetic field with time to induce induced current in the rotor and rotate the rotor by providing the rotor with a rotation torque caused by Lorentz interaction between the induced current and the magnetic field applied to the rotor;

detecting rotation of the rotor; and detecting dynamic property of the sample to detect viscosity and/or elasticity of the sample being in contact with the rotor based on the rotation torque and the rotational movement of the rotor.

12. The method of detecting viscosity and/or elasticity according to claim 11, wherein the rotation control includes rotating the rotor, the rotation detection includes detecting a rotation frequency of the rotor, and viscosity of the sample is detected based on the rotation torque and the rotation frequency.

13. The method of detecting viscosity and/or elasticity according to claim 11, wherein the rotation control includes rotating the rotor from an initial static position before being provided with the rotation torque to an equilibrium static position at which the rotor stops by the balance of the rotation torque and elastic resistance of the sample;

the rotation detection includes detecting a rotation angle from the initial static position to the equilibrium static position; and the dynamic property detection includes detecting elasticity of the sample being in contact with the rotor based on the rotation torque and the rotation angle of the rotor.

14. The method of detecting viscosity and/or elasticity according to claim 12, further comprising preparing standard data obtained by preliminary measuring relationships between rotation torques and rotation frequencies of the rotor in a plurality of materials having known viscosities, wherein the viscosity of the sample is detected by comparing the standard data and a relationship between rotation torque and rotation frequency of the rotor in the sample.

15. The method of detecting viscosity and/or elasticity according to claim 13, further comprising preparing standard data by preliminary measurement of relationships between rotation torques and rotation angles of the rotor in a plurality of materials having known elasticities, and the elasticity of the sample is detected by comparing the standard data and a detected relation between rotation torque and a rotation angle of the rotor in a sample.

16. The method of detecting viscosity and/or elasticity according to claim 11, wherein the magnetic field is controlled to be a rotational magnetic field where a horizontal direction of the magnetic field rotates with time.

17. The method of detecting viscosity and/or elasticity according to claim 11, wherein the rotor is made of a material having a specific weight larger than a specific weight of the sample.

* * * * *